US008383100B2

(12) United States Patent
Villani (10) Patent No.: US 8,383,100 B2
(45) Date of Patent: *Feb. 26, 2013

(54) METHOD TO TREAT AND PREVENT SKIN DISEASES WITH PORIFERA-BASED THERAPEUTIC COMPOSITIONS TREATING AND PREVENTING SKIN DISEASES

(76) Inventor: Maria Villani, Newport Beach, CA (US)

( * ) Notice: Subject to any disclaimer, the term of this patent is extended or adjusted under 35 U.S.C. 154(b) by 594 days.

This patent is subject to a terminal disclaimer.

(21) Appl. No.: 12/543,843

(22) Filed: Aug. 19, 2009

(65) Prior Publication Data

US 2010/0297095 A1 Nov. 25, 2010

Related U.S. Application Data

(63) Continuation of application No. 10/659,451, filed on Sep. 9, 2003, now Pat. No. 7,604,821, which is a continuation-in-part of application No. 10/186,996, filed on Jul. 1, 2002, now abandoned.

(51) Int. Cl.
*A61K 38/43* (2006.01)
*A61K 35/56* (2006.01)
(52) U.S. Cl. ...................... 424/94.1; 424/520
(58) Field of Classification Search ............. 424/94.1, 424/520
See application file for complete search history.

(56) References Cited

U.S. PATENT DOCUMENTS

| | | | |
|---|---|---|---|
| 3,896,238 | A | 7/1975 | Smith |
| 5,139,771 | A | 8/1992 | Gerstein |
| 5,196,185 | A | 3/1993 | Silver |
| 5,538,740 | A | 7/1996 | Abad |
| 5,695,857 | A | 12/1997 | Burreli |
| 5,741,482 | A | 4/1998 | Modi |
| 5,785,978 | A | 7/1998 | Porter |
| 5,869,062 | A | 2/1999 | Oliver |
| 6,106,818 | A | 8/2000 | Dulog |
| 6,136,329 | A | 10/2000 | Boratyn |
| 6,218,345 | B1 | 4/2001 | Brooks |
| 6,312,678 | B1 | 11/2001 | Elliott |
| 6,352,685 | B2 | 3/2002 | Hoshino |
| 6,821,264 | B1 | 11/2004 | Khurana |
| 7,078,047 | B2 | 7/2006 | Philippe et al. |
| 7,604,821 | B2 * | 10/2009 | Villani ............ 424/520 |
| 2004/0109872 | A1 | 6/2004 | Villani |

FOREIGN PATENT DOCUMENTS

| | | |
|---|---|---|
| CN | 1096205 | 12/1994 |
| CN | 1152455 | 6/1997 |
| DE | 4028622 | 3/1992 |
| DE | 10010113 | 8/2009 |
| FR | 2801314 | 5/2001 |
| RU | 2038070 | 6/1995 |
| RU | 2160089 | 10/2000 |
| RU | 2176511 | 12/2001 |
| RU | 2182820 | 5/2002 |
| RU | 2182821 | 5/2002 |
| RU | 2183967 | 6/2002 |

OTHER PUBLICATIONS

Sipkema, D. et al. Marine Sponges as Pharmacy, Marine Biotechnology, vol. 7, pp. 142-162.
Schroder 1942, Use of Fresh Water Sponges in Ukraine, "Die Venvendung derSusswasserschwamme in der Ukraine", Die 3, Umschau Wissenschaft Technik 46: 507-509. Issue 34, pp. 507-509. English translation by USPTO.
REKA Farm, Printed from http://www.reka-farm.ru/prod_e.htm Apr. 28, 2008 4:53:43 PM.
Mankoni et al. 2008. Global diversity of sponges (Porifera: Spongillina) in freshwater, Hydrobiologica, vol. 595, pp. 27-33).
Rozentul, M.A., Handbook an Cosmetics, Medtsina 1964, Moscow, p. 77 (Original Russian and English translation).
Eulenburg, A & M.i. Afanaasiev, Fresh Water Sponge ("BADYAGA"), Real Encyclopedia of Medical Sciences, vol. 1, pp. 656-657 (1891).
Fresh Water Sponge ("BADYAGA"), Encyclopedia Dictionary, vol. 11-A, pp. 676 (1891).
Old Remedy for Theumatoid Pain, Dr. Uzhegov's Handbook of Folk Medicine for Children, pp. 326-327 (1996).
Fresh Water Sponge ("BADYAGA"), Big Encyclopedia of Medicine, vol. 6, 3rd Ed. pp. 563 (1977).
Fresh Water Sponge, Encyclopedia of Medicinal Plants an Animal Products, pp. 352 (1999).
Swatschek, D. Marine Sponge Collagen: Isolation, Characterization, and Effects on the Skin Parameters Surface-pH, Moisture and Sebum. European J. Pharmaceutics and Biopharmaceutics, Jan. 2002, vol. 53, Issue 1, pp. 107-113, abstract only.
Swatschek, D., Microparticies derived from marine sponge collage (SCMPs); preparation, characterization and suitability for dermal delivery of all-Otrans retinol. European J. Pharmaceutics and Biopharmaceutics, Sep. 2002, Vo. 54, Issue 2, pp. 125-133, abstract only.

* cited by examiner

*Primary Examiner* — Ralph Gitomer
*Assistant Examiner* — Kailash C Srivastava
(74) *Attorney, Agent, or Firm* — K&L Gates LLP; Louis C. Cullman; Michelle Glasky Bergman (57) ABSTRACT

Methods to treat skin conditions and diseases by applying Porifera based compositions to the skin are described. Treatable skin conditions and diseases include acne vulgaris, rosacea, seborrheic dermatitis, atopic dermatitis, psoriasis, photoaging, actinic keratosis and eczema, also known as atopic dermatitis. Therapeutic compositions are obtained from members of Porifera, for example sponges, specifically, fresh water sponges. An example of a fresh water sponge is *Spongilla* species. One specific therapeutic composition is obtained from *Spongilla* species and formulated with pharmaceutical excipients.

11 Claims, 3 Drawing Sheets

METHOD TO TREAT AND PREVENT SKIN DISEASES WITH PORIFERA-BASED THERAPEUTIC COMPOSITIONS TREATING AND PREVENTING SKIN DISEASES

RELATED APPLICATION

The present application is a continuation of U.S. patent application Ser. No. 10/659,451 filed Sep. 9, 2003, which is a continuation-in-part of U.S. patent application Ser. No. 10/186,996 filed Jul. 1, 2002, now abandoned, which is hereby incorporated by reference.

FIELD OF THE INVENTION

The present invention is directed to therapeutic compositions suitable for treating skin diseases. Specifically, the therapeutic compositions of the present invention are derived from the Eukayote phylum Porifera. The therapeutic compositions of the present invention can be applied topically for the treatment of various skin disorders and diseases.

BACKGROUND OF THE INVENTION

Skin diseases remain a significant medical and social problem throughout the world. The most common, and therefore the most significant skin diseases, include acne vulgaris, rosacea, seborrheic dermatitis, eczema (atopic dermatitis), psoriasis, photo-aging and actinic keratosis. These skin diseases combine to account for billions of dollars in medical treatments and untold emotional suffering. The emotional impact of skin disease is particularly relevant because patients become easy prey for unscrupulous practitioners and treatment regimes of questionable efficacy. Over the last one hundred years significant advances in pharmaceuticals and dermatological procedures have greatly reduced the severity and frequency of skin diseases. However, many patients do not comply with the often complex and tedious treatment protocols their practitioners prescribe. Moreover, the long-term use of antibiotics has resulted in increased microbial resistance of the bacteria responsible for various skin diseases. Additionally, other chemotherapies can be extremely toxic and have long term deleterious effects on the patient's health and skin. Therefore, alternative therapies for treating skin disorders that are safe, effective and easy to use are urgently needed.

Acne vulgaris is the most common of all skin disorders that affects 85% of teenagers. Nearly 80 percent of the population experience acne at some point in their lives. Moreover, in addition to being a serious medical condition, acne inflicts a heavy emotional and psychological burden on its victims. Marion Sulzberger, MD, one of the founding figures of modern dermatology, wrote in 1948 "there is no single disease which causes more psychic trauma, nor maladjustment between parents and children, more general insecurity and feelings of inferiority and general sums of psychic suffering than does acne vulgaris." The impact can be devastating, leading to depression and even to thoughts of suicide. A survey of 1,985 people by the ASG revealed that three out of four people with acne felt depressed and almost half felt anxious. Research by William Cunliffe, MD, in the United Kingdom, showed that patients with acne had a higher unemployment rate than age- and sex-matched controls. More than a third felt they would have a better job if they didn't have acne, the survey revealed.

Acne is a chronic disease involving the pilosebaceous follicles. Sebaceous glands are found most abundantly on the face and scalp, though they are present on every part of the skin except the palms of the hands and soles of the feet. Cutaneous disorders attributed to the sebaceous gland are really disorders of the entire pilosebaceous unit. The areas most commonly involved in acne are the face, upper chest, and back. Other less common areas include the upper arms, buttocks, and upper thighs.

Acne vulgaris evolves within the pilosebaceous unit via a multifactorial pathogenesis. The central pathogenic factors in acne include excessive sebum production secondary to androgen stimulation, outlet obstruction of the sebaceous follicle arising from excess production of keratinocytes (the basic cell of the epidermis), proliferation of *Propionibacterium acnes* and inflammation following chemotaxis and the release of various proinflammatory mediators.

During the prepubertal period the increase in adrenal androgens triggers the enlargement of the sebaceous glands. These enlarged sebaceous glands produce increased amounts of sebum, which flows through the canal of the sebaceous follicle. This canal is lined with a keratinizing epithelium. In acne patients, there is increased production of the follicular corneocytes lining the follicle and retention of these corneocytes within the follicle. The abnormally desquamated corneocytes and the excess sebum build up within the follicle to form a microscopic, bulging mass. This enclosed, sebum-rich environment is ideal for the proliferation of *P. acnes*, the anaerobic bacterium that produces chemotactic factors and recruits proinflammatory molecules involved in the inflammatory phase of acne. Obstruction of the sebaceous follicle, the primary pathologic event in acne, is giving rise to the micro-comedo, the precursor of all acne lesions. It is a microscopic, bulging mass that results from a combination of hyperproliferative corneocytes and sebum and leads to follicular plugging.

Once the follicle is plugged, its lower portion becomes engorged and distended with sebaceous discharge and keratinocytes. While the pore opening remains closed, the lesion is called a closed comedo, or "whitehead." It is a noninflammatory lesion that evolves from the microcomedo and appears as a white dot ranging from 0.1 to 3.0 mm in diameter and very slightly raised.

Oxidization occurs when the follicle enlarges enough to stretch the pore and the trapped matter is exposed to air. This causes the characteristic dark appearance of open comedones or "blackheads." Open comedone is a noninflammatory lesion that appears as flat or slightly raised, brown-to-black color, about 3-5 mm in diameter.

Early acne, involving a majority of open and closed comedones, is a noninflammatory process. As dilation of the follicle continues, the follicular epithelium is disrupted and irritants such as sebum, hair, and keratinocytes are released into the surrounding dermis. This leakage causes an inflammatory reaction and initiates the formation of the inflammatory lesion papules, pustules, and nodules. Although *P. acnes* is a live bacterium, living in the follicle, it dies when the follicular structure is disrupted. Toxins are released into the dermis, which increases inflammation. Therefore, uncomplicated, inflammatory acne is a sterile process and not a skin infection. As inflammation continues to worsen, larger papules and pustules are created. A papule is a pink-to-red, raised, palpable lesion with no visible accumulation of fluid, which can range from 1 to 4 mm in diameter.

A pustule is a raised accumulation of purulent material on the skin's surface, and is similar in size to the papule. Pustules are sometimes characterized as superficial or deep. In a superficial pustule there is a localized rupture of the epithelium near the skin surface, and in a deep pustule there is extensive destruction of the entire epithelium. Acne nodules are solid, raised inflammatory lesions that exceed 6-10 mm in diameter and are situated deeper in the dermis. A nodule may persist for weeks. The acne cyst is a large nodule (may be as large as several centimeters in diameter) that has suppurated and become fluctuant. Scars form as a result of damage to the surrounding dermis. Scars may appear as small deep punched out pits ("ice pick"), atrophic macules, hypertrophic papules, or broad, sloping depressions. Darkly pigmented skin affected by acne tends to develop significant postinflammatory hyperpigmentation. This tendency has given rise to the suggestion that a new acne lesion should be designated—the acne hyperpigmented macule (AHM). The AHM can last for four months or longer, and is often the central complaint of acne patients with skin of color.

There is no single standardized grading system for acne, but there are several useful methods used to classify the disease. Most simply, acne is described as mild, moderate, or severe. Because acne is a chronic, emotionally stressful condition that may persist for years, long term therapy is often required. Presently the clinician has numerous treatment options. However, each one has significant adverse qualities and varying degrees of efficacy.

The most commonly used nonprescription topical product is benzoyl peroxide. Benzoyl peroxide (BP) is an antimicrobial that is effective for killing *P acnes*. It usually takes about two weeks to work and it must be used continuously to keep acne at bay. This is because BP does not affect microcomedo formation, sebum production or the way the skin follicle cells are shed, and when patients stop using it, the acne comes back. Benzoyl peroxide is marketed under a variety of trade names in over 200 formulations, including gels, creams, lotions, washes, and bar soaps, in a variety of concentrations (most often 2.5%, 5%, and 10%). If used continuously, it often improves condition for milder cases of acne. Concentration should be chosen accordingly to skin type and tolerance. Side effects consist mainly of skin irritation including burning, blistering, crusting, itching, severe erythema, skin rash, dryness, and chemical imbalance of the skin. Benzoyl peroxide further reduces skin levels of superoxide dismutase, catalase and other skin antioxidants that are important in preventing and healing acne. Moreover, by destroying antioxidants naturally occurring in the skin Benzoyl peroxide promotes premature aging of the skin.

Another nonprescription topical treatment is salicylic acid. Salicylic acid helps to correct the abnormal shedding of cells and is useful in treating milder acne. Salicylic acid helps unclog pores to resolve and prevent lesions. However, salicylic acid does not inhibit sebum production or possess antimicrobial properties. The patient must use salicylic acid on a regular basis to prevent acne from returning. Salicylic acid is available in many acne products, including lotions, creams, washes, gels, and pads.

In many cases over-the-counter (OTC) preparations are not effective and must be used in combination with prescription drugs. Antibiotics are the most commonly prescribed class of anti-acne medications. Antibiotics work inhibiting the growth of *P. acnes* and may be applied topically or taken systemically. The most widely prescribed topical antibiotics are erythromycin and clindamycin. Topical antibiotics are limited in their ability to penetrate the skin and clear more deep-seated *P. acnes* and do not inhibit comedo formation alone and thus must be used in combination therapies.

Systemic antibiotics circulate throughout the body and into sebaceous glands. Systemic antibiotics are used to treat severe acne but generally have more side effects than topically applied medications. They also do not address the other causative factors in acne and may take several weeks or months to clear up acne. Oral antibiotics are usually used in combination with other drugs that "unclog" follicles such as salicylic acid. However, systemic antibiotic therapy is incompatible with pregnancy and some may reduce the effectiveness of oral contraception pills, risking a pregnancy during treatment.

The front-line oral antibiotics for the treatment of acne are the tetracyclines. Tetracycline cannot be taken with food containing divalent cations such as calcium and iron and predispose patient to severe sunburn or a pruritic rash due to its photosynthesizing qualities. All tetracyclines are contraindicated in pregnancy and in children who have not yet formed their permanent teeth (risk of discoloration). Additionally tetracycline call antibiotics often cause esophageal irritation. Side effects of minocycline (a commonly prescribed synthetic tetracycline) may include vertigo, blue-gray discoloration of the skin and teeth, and a lupus-like syndrome.

Erythromycin has long been considered the preferred second-line oral antibiotic for acne therapy. It does have an excellent side-effect profile (with gastrointestinal upset generally the most common problem) and may be approved for use even in pregnant women. However, antimicrobial resistance is a major problem associated with all antibiotics commonly used to treat acne and this is most pronounced with erythromycin. The emergence of antibiotic-resistant *P. acnes* is an issue of increasing concern with both topical and oral antibiotics in the treatment of acne. Over the past 25 years, laboratory studies have demonstrated a rapidly increasing pattern of *P acnes* resistance to antibiotics, especially erythromycin (published studies indicate that the overall incidence of antibiotic-resistant *P. acnes* has increased from 20% in 1978 to 62% in 1996). Bacterial resistance is diminishing the effectiveness of current acne therapies and threatens to limit the options available to heal the most common skin condition diagnosed and treated by physicians. Antibiotic resistance in acne treatment is a global problem as antibiotic-resistant strains of *P. acnes* have been reported in the United Kingdom, Germany, France, Japan, and the United States.

Vitamin A derivatives or "retinoids" are being used with increased frequency as topical treatments for moderate to severe acne. The topical retinoids include vitamin A acid (tretinoin), its analogs, and newer agents that bind to and activate retinoid receptors. Topical retinoid preparations help to unclog pores and normalize skin growth and shedding. However, topical retinoids can cause severe skin irritation and therefore require titration at the initiation of therapy to allow patients to adjust. Moreover, topical retinoids and retinoid analogs pose a risk of teratogenicity. For example, Tazarotene is a pregnancy category X drug and should not be used in pregnant women.

Recently, the FDA has approved the oral retinoid Isotretinoin (Accutane). Accutane is recommended for patients who have severe scarring and cystic acne. Accutane is anti-inflammatory and decreases the size of the sebaceous glands, thus decreasing the amount of sebum produced and causes long-term acne remission and reduces scarring. Accutane is treatment is indicated if less than 50% improvement in acne severity is observed after 6 months of treatment with combination topical and oral therapy, the appearance of scar, acne that is associated with significant psychological distress or acne that quickly relapses during or shortly after conventional therapy. However, Accutane has many adverse reactions, including hepatotoxicity, increased levels of triglycerides, pancreatitis, and hypercalcemia with loss of bone mass. Moreover, Accutane is teratogenic. Consequently, the FDA mandated that women undergoing Accutane therapy must use two forms of birth control. Moreover, recently Accutane has been linked to depression and suicide. Parents are required to sign a consent form asserting their understanding of this possibility and should be cautioned to carefully monitor the emotional status of teens being treated with Accutane.

Anti-inflammatory medications called corticosteroids may be injected by a dermatologist directly into severe inflamed acne lesions to help heal existing lesions. However, these do not prevent development of new acne and may leave a permanent hardening in the place of injection.

Acne vulgaris is a chronic dermatologic disorder that must be treated consistently. It is not unusual that traditional topical therapy will initially worsen acne due to irritating, sensitizing, and toxic properties of the chemical therapeutic agents. This initial response usually lasts 2 to 4 weeks. Since it takes about 28 days to regenerate skin, the effect of medications does not appear immediately. Improvement, if any, becomes noticeable after 4 to 8 weeks of therapy. The maximum benefit of systemic agents, such as oral contraceptives, on acne occurs not earlier than in 3-4 months.

Many OTC preparations are toxic for the skin enzymes, which makes them automatically toxic for the skin overall. Intracellular and extracellular enzymes that found in the skin are essential for healthy skin condition, right pH and skin protective capability against pathogens. The consequences of an impairment of enzymes, even through the inactivation of trace elements that primary act for enzyme performance, cannot be evidence after one or a few applications but only following repeated treatments, for example as in the case with Benzoyl Peroxide preparations for acne prone skin, which might be applied several times a day for many years.

A non-compliance with anti-acne regime is one of the major reasons for treatment failure among patients with acne vulgaris. Motivating patients to adhere to treatment, especially during the maintenance phase, remains a challenge. A recent randomized, controlled study involving young adults with acne vulgaris evaluated the efficacy of various non-pharmacologic interventions for enhancing adherence to benzoyl peroxide. Adherence was measured through a combination of patient self-report and the return of self-monitoring cards. The overall adherence rate after 3 months was 48%. The study found that 52% of patients were noncompliant. They did not exactly follow the directives of their dermatologists due to the complexity of the regime.

Both researchers and practicing clinicians concur that the simpler the medication regimen for acne patients, the better the adherence. To improve the compliance among this group of the patients, effective, well tolerated, and simplified regime is needed.

Although acne is the most common skin disease and one with the greatest economical and sociological significance, it is not the only skin disorder that can benefit from improved therapeutic regimes and compositions. For example rosacea, seborrheic dermatitis, eczema (atopic dermatitis), psoriasis, photo-aging, actinic keratosis, and great number of other bacterial, viral, and fungal diseases as well as skin pigmentation disorders are also significant health and cosmetic problems requiring improved therapies with simplified regimes.

The Holy Grail of medicine would be to slow or reverse the aging process. Aging is a complex process that is largely determined genetically. However, free radical damage caused by reactive oxygen species contributes significantly to the aging process. One manifestation of free radical-associated aging are so-called "age spots." Age spots are actually the accumulation of special pigments called lipofuscin, a brown waste, that accumulates in the skin in highly damaged areas.

Protection against free radical-associated oxidative damage includes the activation of water-soluble reductants in the cytosol, lipid-soluble antioxidants residing in cellular membranes, and the antioxidant enzymes, superoxide dismutase, catalase, ascorbate peroxidase, glutathione peroxidase and glutathione reductase. Biogenic production of free radicals occurs mostly during normal processes of cellular metabolism. A by-product of energy metabolism is the uncoupling of electrons in the transport chain to generate superoxide, via activation of molecular oxygen, leading to the production of hydrogen peroxide and the supra-reactive hydroxyl radical. Such reactive oxygen species (ROS) are highly damaging to DNA, proteins and membrane lipids causing cellular impairment. In the normal condition of aging, antioxidant functions decline to further accelerate the aging process, and this exacerbates the progression of age-related degenerative diseases. Therefore, preventing or decreasing the formation of reactive oxidants in metabolic electron transport presents a clear strategy for reducing cellular oxidative stress and rate of aging.

Free radical damage has also been implicated as a cause, or exacerbating factor in eczema. A recent university sponsored study examined the levels of lipid peroxidation in erythrocytes, some parameters of the antioxidant system and the activity of lysosomal enzymes in eczema patients of mix origin (exo/endogenous). The results of the study reveal an intensification of erythrocyte lipid peroxidation and a depression of antioxidant protection. This imbalance of lipid peroxidation/antioxidant systems induces modifications in biomembrane's structure, especially lysosomal ones. That follows to an increase of the lysosomal intracellular activity and then to a lysosomal penetration in blood circulation and facilitates cutaneous inflammatory manifestations. So, the complex treatment of eczema must include an antioxidant therapy and a pharmacological stabilization of lysosomal membranes.

The Department of Dermatology and Skin Ageing, and Cancer Research Centre of University Pavia in Italy studied the activity of 14 enzymes, representative of the main metabolic pathways in epidermis of 63 normal human subjects ranging in age from 1 month to 90 years. No difference of activity was observed in any of the enzymes studied despite the varied age. The lack of influence of age on the activity of the enzymes in human epidermis enhances the significance of the variations, which are reported in pathological conditions like psoriasis, chronic sun-damaged skin and neoplasm.

In addition, enzyme activity depression in chronically sun-exposed skin has a significantly contributes to neoplasm formation. This is clearly evidenced by the fact that the areas usually exposed to the sun's rays (e.g., face, back of hands) are 100 times higher than on the skin of unexposed areas (e.g., abdomen). This leads one to regard chronic sun damage as a precancerous state. Chronic exposure to ultraviolet (UV) light is the leading cause of extrinsic aging, or alterations of the skin due to environmental exposure. Estimates indicate that almost half of a person's UV exposure occurs by age 18. Photo aging causes numerous histological, physiologic, biochemical and clinical changes.

One of the manifestation of aging skin is decreased ability to shed dead cells, resulting in various unsightly skin conditions. The mainstay of topical therapy of photo-aging skin continues to be chemical peels. A chemical peel is a procedure in which a topically applied wounding agent creates smooth, rejuvenated skin by way of an organized repair process. Complications of chemical resurfacing, including permanent sequelae, such as pigmentary dyschromias, infection, or scarring, may occur even though a controlled chemical wound induced.

Therefore, there remains a need for therapeutic topical compositions that are safe, effective, possess multifaceted mechanisms of action and are conducive to patient compliance.

SUMMARY OF THE INVENTION

The present invention relates to novel skin care therapeutics derived from invertebrate species of the phylum Porifera. Poriferans are commonly referred to as sponges. An early branching event in the history of animals separated the sponges from other metazoans. Fossil sponges date from the late Precambrian period are among the oldest known animals and account for over 900 fossil genera. The approximately 5,000 living sponge species are classified in the phylum Porifera, which is composed of three distinct groups, the Hexactinellida (glass sponges), the Demospongia, and the Calcarea (calcareous sponges).

The skin care therapeutic compositions of the present invention are useful in treating and preventing a wide variety of skin conditions including, but not limited to, acne vulgaris, rosacea, seborrheic dermatitis, eczema (atopic dermatitis), psoriasis, photo-aging and actinic keratosis. Moreover, the skin care therapeutics of the present invention are useful as skin resurfacing compositions, treatments for oily skin, and as deep peeling treatments. In an exemplary embodiment the compositions of the present invention are applied topically. The topical applications can be applied monthly, weekly, daily or multiple times daily depending on the condition to be treated and extent of disease progression. Moreover, the compositions of the present invention can be applied in combination with other topical or systemic therapies.

In one embodiment of the present invention the skin care therapeutics are derived from the Porifera Subphylum Cellularia, Class Demospongiae, Subclass Ceractinomorpha, Order Haplosclerida Family Spongillidae Genus *Spongilla*.

In one embodiment of the present invention the Porifera is harvested from marine water sources including but not limited to salt water lakes, oceans and inland seas.

In another embodiment of the present invention the Porifera is harvested from fresh sources such as rivers, lakes, ponds and streams.

In yet another embodiment of the fresh water source is located in Eurasia, specifically the Russian Federation.

In another embodiment of the present invention a topical skin care therapeutic is made from powdered Spongilla.

In yet another embodiment of the present invention a topical skin care therapeutic is made from powdered fresh water sponges selected from the group consisting *Spongilla lacustris* L., *Spongilla. fragilis* Leidy, and *Ephydatia fluviatilis*.

In another embodiment of the present invention the powdered Spongilla is compounded with other active and inactive ingredients. Ingredients include, but are not limited to antibiotics, anti-inflammatories, antiseptics (such as, but not limited to, hydrogen peroxide and boric acid), anesthetics, coral powder, white seaweed powder, green seaweed powder, enzyme gel, jojoba oil. The Spongilla powder is present in the amount of from approximately 0.1% to 100% Spongilla powder.

In another embodiment of the present invention the inactive ingredients include water selected from the group consisting of water for injection, distilled water, deionized water, chamomile water and calendula water.

In another embodiment of the present invention the inactive ingredients includes pharmaceutically acceptable diluents, fragrance, coloring and emollients.

In yet another embodiment of the present invention the therapeutic composition comprises from 1 to 1.5 grams of substantially pure Spongilla powder, and at least one additional excipient selected from the group consisting of from 0.1 to 0.5 grams of green seaweed powder, from 0.1 to 0.5 grams of white seaweed powder, from 0.1 to 5 grams of 0.2 grams of coral powder, from 0.5 mL to 5 mL of 0.1% to 10% hydrogen peroxide, from 0.5 mL to 5 mL of 0.1% to 10% boric acid and from 0.5 to 10 mL of water.

Other embodiments and characteristics of the invention will appear in the course of the description and examples that follow.

DETAILED DESCRIPTION OF THE INVENTION

Natural Marine Products are relatively new and have become a active area of research for new industrial chemicals, biologics and chemotherapeutics. Natural Marine Products Chemistry is a critical part of this research and is responsible for the isolation and Identification of the vast array of novel molecules produced by marine organisms. Many of these molecules possess structural features that are unique to marine organisms and result from the unique aquatic environment (high level of halogens and nitrogen) in which the host organisms live. There is mounting evidence that many of the natural products isolated from marine organisms may be derived from symbiotic microorganisms residing within the marine organisms.

Biologically active metabolites are produced by organisms for a range of purposes including relief from environmental stress, chemical signaling, and aggression among species. These natural processes can inform the search for functional bio molecules directed towards specific applications. For example, new sunscreen products were discovered through basic research into the tolerance of reef corals to ultra-violet radiation.

Sponges are multicellular marine animals belonging to a large group of simple animal species known as invertebrates. Sponges originated billions of years ago and are among the oldest animals on earth. Presently, approximately 5,000 species of Sponges are known. Sponges are composed of a soft tissue suspended in a jelly-like proteinaceous matrix supported by a hard skeleton composed of needle-like structures known as spicules. Spicules are primarily composed of calcium carbonate, or silica and collagen.

Sponges belong to phylum Porifera, a highly primitive group with no tissue grade of organization. The stiff body houses numerous channels and pores allowing currents of fresh water to enter. The largest in current pores are known as oscula, and the smallest are ostia. Food-bearing water flows into the sponge through the ostia in its mound-like body and out through osculum. Water is encouraged to flow within the sponge by the action of flagellated choanocytes. Choanocytes also constitute the filter-feeding apparatus, trapping suspended food particles as they pass along the series of internal channels. Because sponges are essentially sessile, they are heavily reliant upon the effectiveness of their cell-lined channels in trapping food, oxygen uptake and removal of waste products. Sponges are highly susceptible to pollution and release of suspended sediments which block up their delicate system of tubes and pores, thus preventing basic body functions. Sponges have great powers of regeneration from injury or predation.

Two reproductive processes are known to occur in the sponges: the one of them, asexual, and the other, truly sexual. In the common fresh-water Sponges, towards the autumn, the deeper layer of the sponge becomes full of exceedingly small bodies, sometimes called "seeds" or "gemmules." The whole Sponge dies down, and the seeds, enclosed in their case, remain uninjured through the winter. At the springtime, the encysted masses of sponge particles stimulated by the altered temperature of the water, creep out of their "seeds", and grow up into Sponge.

The success rate of finding a new active chemical in marine organisms is 500 times higher than from terrestrial sources. Sponges have proven to be a prolific source of novel therapeutic agents, often with biomedical action superior to that of existing pharmaceuticals. Drug discovery from sponge colonies is now a major focus of the pharmaceutical and biotechnology industries. However, the primary area of concern about this new source of therapeutics is the question of their supply and difficulties of culturing sponges and their symbionts in the lab. The reliability and reproducibility of material from natural sources is also critical, because seasonal and environmental changes interfere with the chemical composition and biological properties of natural samples. Furthermore, biologically active molecules are expected to be produced only temporarily as a response of specific environmental stress. Extracting sufficient quantities of the active chemical from the natural source just for completion one clinical study requires many tons of sponge colonies and as a result is not a viable option for worldwide distribution. Therefore, while marine biotechnology presents tremendous potential for new pharmaceuticals, commercial success is minimal to none.

Nevertheless, like many natural products, sponges have been used in homeopathy and other forms of natural medicine for centuries. Eastern Europe and Eurasia have a long history of preparing tinctures and powders from aquatic animals including fresh water sponges. Folk medicines known collectively as "Bardiaga" refer to powdered fresh water sponges and used for medicinal purposes. Russian folklore and homeopathic teachings suggest that Bardiaga is useful for treating such diverse syndromes as bruising arthritis and rheumatism.

Bath sponges (*Spongia officinalis*) have also been used for centuries for cleaning wounds, for contraception and even as implants after breast cancer operations. Furthermore, folk medicine and natural medicine literature is replete with diverse preparations made from dried sponges and used to treat and palliate myriad diseases. The oldest medicinal sponge preparation in recorded history is dried and burned *S. officinalis* is offered as a treatment for goiter and thyroid-related diseases. The unusually high concentration of iodine in *S. officinalis* made is a uniquely effective folk remedy.

Since sponges are essentially non-motile animals that are highly susceptible to predators and changes in their microenvironments, they have evolved an elaborate bio-defense system that includes a cornucopia of biologically active (bioactive) compounds. Today, it is believed that many of these sponge-derived bioactive compounds possess cytotoxic, antibiotic, anti-viral, anti-inflammatory, and anti-fouling properties. However, most of these bioactive compounds remain uncharacterized. Furthermore, as discussed above, these bioactive compounds are produced in extremely low concentrations on a weight percent basis and therefore their isolation in pure form would require the harvesting and processing of literally tons of sponges. Many of these bioactive compounds may derive their efficacy through naturally synergistic and complementary mechanisms that would be lost if purified and studied in isolation. Therefore, the present inventor has invented the technology of development Porifera species compositions, their formulation and applications that eliminates the need to purify and characterize individual bioactive compounds, maintains the integrity of their potentially synergistic properties and resolves the problems of supply and environmental impact.

Fresh water sponges including, but not limited to, *Spongilla lacustris* L., *Spongilla fragilis* Leidy, and *Ephydatia fluviatilis*, are not presently used to provide pharmaceutical compositions that have undergone rigorous safety and efficacy testing. The present inventor has discovered that Poriferans can be natural sources of complex biologicals that provide new compositions useful for treating, palliating and preventing a variety of diseases, including, but not limited to, acne vulgaris, rosacea, seborrheic dermatitis, eczema (atopic dermatitis), psoriasis, photo-aging and actinic keratosis. The synergetic poly-pharmacy of these complex biologicals has advantages over synthetic single-ingredient drugs by providing greater therapeutic benefit and less overall toxicity. Specifically, and not intended as a limitation, but merely as an exemplary embodiment of the invention, the present inventor has developed therapeutic compositions derived form the fresh water sponge species *Spongilla lacustris* L.

In one embodiment of the present invention an anti-acne vulgaris therapeutic is provided that effectively treats, palliates, and in some cases prevents the most important pathological factors in acne development. These pathological factors include excessive sebum production, excess production of keratinocytes, outlet obstruction of the sebaceous follicle, *P. acnes* proliferation and inflammation. Furthermore, the anti-acne preparations of the present invention are conducive to therapeutic regimes and are non-toxic when used as directed. The topical anti-acne preparations of the present invention can be used alone, or in combination with other topical or systemic therapeutics.

As discussed above, acne vulgaris is a common, multifactorial inflammatory disease of the pilosebaceous duct. *Propionibacterium acnes* proliferated in sebum, produces chemotactic factors followed by phagocytosis. This process results in the production of reactive oxygen species, which contribute to the inflammatory reaction in papulopustular type acne. The overuse of antibiotics has resulted in the emergence of antibiotic resistant strains of *P. acnes* thus complicating its treatment and prevention. Approximately sixty percent of *P. acnes* are resistant to one or more of the antibiotics typically used to treat acne. Benzyl peroxide, as an alternative treatment, kills *P. acnes* but promotes premature aging of the skin. Furthermore, benzyl peroxide reduces already decreased skin levels of superoxide dismutase, catalase and other skin antioxidants that are important in preventing and healing acne. Consequently, bacterial resistance to currently available anti-acne antibiotics, the deleterious effects of topically applied compounds such as benzyl peroxide and with the increased concern over the serious side effects of oral drugs such as the retinoids, has created a great need for new, safe and effective treatments for acne vulgaris in addition to other skin diseases.

The mechanisms of action associated with the novel anti-acne therapeutics of the present invention are multi-faceted. Like most complex biological therapeutics such as low molecular weight heparin preparations (e.g., enoxaparin, sodium), the exact mechanism of action of the present compositions are not fully known. However, the present inventor believes, without being bound to these theories, that the active ingredients of the anti-acne preparations disclosed herein act synergistically via one or more of following mechanisms. The present invention stimulates a localized histamine reaction that dilates blood vessels thus increasing blood flow to the treatment area. This results in increased amounts of oxygen, nutrients, and antibodies reaching the skin cells. Due to the stimulation of blood circulation and lymphatic drainage, the removal of excess fluid, bacteria, and debris is increased. Moreover, the topical therapeutics of the present invention dissolve excess sebum, reduces sebum production, and makes the excreted sebum less sticky. This prevents occlusion of the pores and consequent formation of comedones. Furthermore, refined organic residue, such as, but not limited to skeletal spicules mechanically separate epidermis surface layers reduces the keratinocytes cohesion thereby increasing stratum corneum sloughing and sebum plug and loose keratinocyte removal, which opens pores and prevents future occlusion and consequent formation of comedones. Naturally occurring antibiotic compounds kill bacteria causing acne. Natural steroids reduce inflammation. Also it may act as a vasodilator and improve local microcirculation. Continuous use the topical therapeutics of the present invention may reduce skin fatty acid concentrations and normalize keratin turnover in the sebaceous follicles. Furthermore, significant clinical evidence supports the conclusion that the therapeutic preparations of the present invention also produce direct and indirect anti-inflammatory effect.

Multiple acne infections over time change the chemical balance of the skin and ultimately change the balance of the body's chemistry. For example, people with moderate to severe acne have significantly less zinc in their body than people their ages that do not have acne. Furthermore, chronic acne sufferers have skin that is uniquely deficient in linoleic acid and protective antioxidants.

The present invention corrects the above imbalances allowing the skin's immune processes to effectively control bacteria and prevent infections. Accordingly, in one embodiment of the present invention compositions are prepared having high bioactivity and contain high concentrations of zinc, linoleic acid, antioxidants, calcium and other biochemicals that act to block the conditions that lead to acne and facilitate the healing.

When used as a peeling agent, the present invention rejuvenates the skin, stimulates new cell growth, elastin and collagen production and improves skin tone and texture. The enzymes contained in the compositions dissolve and digest old, debilitated or dead cells from the skin's outer layer without harming the younger, living cells and result in softer, smoother skin. Overall, the compositions help to dissolve stagnant spots, infiltrates, remove superficial scars comedones, regulate skin pH and sebum production and prevent further acne eruption and scar formation.

The present inventor has demonstrated that the compositions disclosed herein are effective in treating mild, moderate, and severe acne, rosacea, seborrheic dermatitis, eczema (atopic dermatitis), photo-aging and actinic keratosis. Furthermore, the compositions of the present invention can be used safely with traditional therapies for acne and other dermatological diseases including but not limited to traditional antimicrobial scrubs, astringents, salicylic acid preparations and systemic therapeutics including but not limited to antibiotics and anti-inflammatory prescription drugs.

Over-the-counter preparations and prescription pharmaceutical preparations of the present invention are both considered within the scope of the present invention. Moreover, the compositions of the present invention are presently undergoing clinical trials and are intended for use in a professional environment administered and used under the direction of a qualified physician. As such the compositions of the present invention may also include instructions for use and product labeling approved by the United States Food and Drug Administration (USFDA) and other healthcare regulatory agencies world-wide. In one embodiment of the present invention product labeling and instructions for use that comply with all applicable sections of 21 U.S.C. Chapter 9, Subchapter V, part A section 352 and section 21 CFR part 201 (hereinafter referred to as FDA approved product labeling and/or package insert) are provided.

Compositions made in accordance with the teachings of the present invention have been analyzed extensively. The desiccated and granulated raw material of the present invention is an odorless, grayish-red non-hygroscopic powder. The powder is partially soluble in water and forms a greenish-red colored solution when mixed in a ratio of 1 part to 3; approximately 50 to 60% percent remains insoluble and comprises the organic fraction providing compositions of the present invention with mechanical-abrasive properties. The pH of the soluble fraction is between approximately 7.0 to 7.5 with a mean pH of 7.35; the specific gravity is between approximately 1.04 to 1.07 with a mean specific gravity of 1.058. Peak absorption is observed at between 210 nm to 250 nm when measured between 200 and 900 nm using methods known to those skilled in the art of physical chemistry.

Table 1 includes a non-limiting representative analysis of the organic and inorganic constituents.

TABLE 1

| Inorganic Component (IC) | IC mg/g of dried raw material | Organic Component (OC) | OC g/110 g of dried raw material | Enzyme Activity (EA) | Units per 100 g |
|---|---|---|---|---|---|
| Sodium | 160-170 | Protein | 1.90-2.00 | Alkaline Phosphatase | 80-90 |
| Potassium | 120-130 | Neutral fats | 1.10-1.20 | Asparagine Transferase | 20-25 |
| Ammonia | 30-40 | Glucose | 0.3-0.4 | Alanine Transaminase | 9-10 |
| Calcium | 160-170 | Steroids | 0.0002 | Gamma-glutamyl Transpeptidase | 7-8 |
| Magnesium | 20-40 | Hydroxy-purines | Trace | Catalase | 50-55 |
| Iron | 320-330 | Total Nitrogen | 0.012-0.014 | Malanic dialdehyde | 0.15-0.2 |
| Copper | 190-200 | | | Superoxide | 6030-6040 |

TABLE 1-continued

| Inorganic Component (IC) | IC mg/g of dried raw material | Organic Component (OC) | OC g/110 g of dried raw material | Enzyme Activity (EA) | Units per 100 g |
|---|---|---|---|---|---|
| | | | | dismutase | |
| Zinc | 11-13 | | | Ceruloplasmin | 450-500 |
| Chlorine | 130-140 | | | | |
| Sulfate | 115-120 | | | | |
| Phosphate | 420-430 | | | | |
| Nitrate | 25-30 | | | | |
| Bicarbonate | 540-550 | | | | |
| Carbonate | 120-125 | | | | |
| Silicates | 13-15 | | | | |

*Ranges are approximate and based on normal laboratory standard deviations for the assay methods employed. Assays were conducted using standard analytical procedures known to those having ordinary skill in the art of analytical chemistry. Enzyme activity is expressed in units of enzyme activity per 100 mg of dried material. Units are based on a recognized International Biological Standard for each assay.

It should be understood by those skilled in the art that the elemental and organic analysis performed on representative samples is not intended to be a comprehensive or even partial listing of the active ingredients found in the compositions of the present invention. As previously discussed, there may be myriad bioactive molecules present in the Porifera products of the present invention that have not been previously identified. The analytical data in Table 1 provides persons skilled in the art non-limiting data that may be useful in characterizing compositions made in accordance with the teachings of the present invention. However, in addition to other possible synergetic and complementary bioactive compounds contained in the present invention the ingredients identified in Table 1 may also provide certain beneficial effects. Without being bound to this theory, the present inventor proposes a possible role for many of the quantified ingredients in Table 1.

The Medical Research Council in Dunn Clinical Nutrition Centre, Cambridge, United Kingdom conducted the study showing dissimilatory nitrate reduction by P. acnes isolated from human faces. Low concentrations of nitrite (ca. 0.2 mM) inhibited growth of P. acnes in culture. The nitrite was slowly reduced to nitrous oxide enabling growth to occur, suggesting that denitrification functions as a detoxification mechanism.

Copper is involved in the production of collagen, the protein responsible for the structural integrity of bone, cartilage, skin, and tendon. It is also involved in the production of elastin, the protein that is mainly responsible for the elastic properties of blood vessels and skin. Studies have proven that copper is also essential to tissue building processes. As we age, our skin thins, and lines and wrinkles develop as our bodies become slower to produce collagen, elastin, and glycosaminoglycan (GAG). GAG functions as cement that bonds tissue components together. Age spots appear and skin becomes dull and lifeless as cell renewal slows and the skin retains less moisture. Scientific studies have demonstrated that copper plays a vital role in skin health, by helping restore the skin's ability to repair itself. Copper is a powerful collagen and elastin promoter and plays an antioxidative role in the body. It is important in the production of GAG. Copper-dependent enzymes increase the benefits of natural tissue building processes.

Zinc, through a group of enzymes called metalloproteinases, breaks down dysfunctional tissues of acne, thereby enabling the infection site to rebuild. Zinc directs the body's T-cells to bacteria and infection by way of a signaling chemical called adenosine deaminase. Zinc is a key element in the production of new skin cells, new collagen and elastin, new blood vessels and other components of the skin. Moderate to severe acne literally consumes the body's supply of zinc, causing the patient to become systemically zinc deficient. When the skin is zinc deficient, the clean up and repair of infections can be slow and possibly incomplete, allowing the potential of scarring. Zinc is especially critical with cystic acne because cystic infections do not discharge waste materials.

Zinc in sufficient amounts and right form acts to prevent acne as well. Testosterone in the skin converts to dihydrotestosterone, which stimulates the production of sebum and contributes to acne. Zinc via 5-alpha-reductase inhibition blocks this conversion and thereby reduces sebum production. Zinc is required in the production of the skin's super antioxidants that reduce the damage of free radicals, reducing inflammation and keeping the healing process moving forward.

Glucocorticoids are widely used for the treatment of various diseases, despite known side effects such as skin atrophy. Many studies have shown that the status of collagen fibers in the skin is affected by glucocorticoid treatment. The results of a study in Japan showed that skin treatment with glucocorticoids strongly interferes with both the synthesis and degradation of type I collagen and, more drastically, type III collagen, the molecule that is known to play a major role in the initiation of wound healing. The study provided a molecular basis for the deterioration of skin function, impaired wound healing, and skin atrophy caused by glucocorticoid treatment. Contrary to experience with synthetic steroids, naturally occurring steroids contained in the present invention provide excellent anti-inflammatory effects without adverse properties described above.

Enzymes are specific biological catalysts in the skin. Failure in the production or activity impairment of a single enzyme leads to metabolic disorders and worsen the acne condition. Since activity of many enzymes is significantly depressed in skin with metabolic diseases, photo-aging and cancer, their presence in therapeutics is the most desirable for the treatment of the above mentioned diseases.

Alkaline Phosphatase (AAP) is a single enzyme of the 'bone-liver-kidney' type, which is present both in a soluble and in membrane-bound form in the skin. It occurs almost exclusively in the dermis, not more than 1% of the total alkaline phosphatase of human skin being present in the epidermis.

In a study that was carried out on leukocyte enzyme activity from prints of skin cut wounds cyto-chemical analysis revealed a rapid increase in enzyme activity in the fourth hour after the wound occurred, which can be explained by the alteration in leukocyte metabolism induced by the damaging agent. Thus suggesting a critical role for AAP in wound healing.

Asparaginase is enzyme that has proved to be particularly promising for the treatment of cancer. Its action depends upon the fact that tumor cells are deficient in aspartate-ammonia ligase activity, which restricts their ability to synthesize the normally non-essential amino acid L-asparagine. Therefore, they are forced to extract it from body fluids. The action of the asparaginase does not affect the functioning of normal cells which are able to synthesize enough for their own requirements, but reduce the free exogenous concentration and so induces a state of fatal starvation in the susceptible tumor cells. A sixty percent incidence of complete remission has been reported in a study of almost 6,000 cases of acute lymphocytic leukemia.

Gamma-glutamyl transpeptidase (GGT) is another enzyme critical in antioxidant and anticancer defense. GGT activity was found in both the epidermis and dermis, the former being more active. GGT is one of the most studied chemicals in cancer chemoprevention, a desirable and important facet of biomedical research.

Superoxide Dismutase (SOD) is the best known and perhaps most important of the antioxidant enzymes. It converts the very harmful free radicals super oxide to the less active peroxide, which is then further converted by other antioxidant enzymes Catalase (CAT) into water. The natural synergetic interaction between these two antioxidant enzymes constitutes the most effective system of free radical control in our bodies. Their combined activity represents a major anti-aging factor. Deficiency in SOD/CAT is the most notorious factor in most inflammatory processes.

Research suggests that SOD may be the most important enzyme involved in free radicals scavenging and marinating cell membrane integrity. Compositions containing SOD/CAT have demonstrated utility as pre- and post operative supplements. When administered to surgical patients significant improvement in recovery rates and reduced convalescent periods have been observed. Moreover, when used as a therapeutic SOD can exert strong regenerative effects on tissues that have become hardened or fibroid because of age, disease, or injury.

In a study conducted by the Department of Dermatology, Suleyman Demirel University Faculty of Medicine, Isparta in Turkey, researchers investigated the role of reactive oxygen species in inflammation of acne by determining the activity of antioxidant defense enzymes in leukocytes. The results showed that activity of SOD was significantly decreased in the acne group. Researchers suggested drugs with antioxidative effects are valuable in treatment of acne patient's, since their antioxidative defense enzymes are severely impaired.

Ceruloplasmin (CP) is a copper-containing protein that is an important extra-cellular antioxidant and free radical scavenger. The liver is the primary organ that expresses CP; however, recent studies have identified the lung as another major site of CP synthesis. Ceruloplasmin plays critical role in host defense against oxidative damage and infection.

In an exemplary embodiment of the present invention the Porifera is used to prepare topical therapeutics is *Spongilla lacustris*. As discussed briefly above, crude preparations of fresh water sponge colonies of mixed genus, including but not limited to *Spongilla lacustris* L., *Spongilla. fragilis* Leidy, and *Ephydatia fluviatilis*, have been used by native people to prepare folk remedies (e.g. Bardiaga) for centuries. However, these crude preparations generally comprise inconsistent mixture of various sponge genus, myriad contaminates including other marine life forms, soil sediment and other debris associated with the Sponges' natural habitat. It is produced without batch-to-batch consistency, necessary for pharmaceuticals. Moreover, sponge colonies were collected randomly without regard to environmental conditions such as, but not limited to, the presence or absence of predators, water temperature and water pressure, oxygen availability, salinity, season and life cycle. Consequently, these compositions, like many other crude natural products were seldom efficacious and often dangerous to use. Unlike crude folk remedies the therapeutic compositions of the present invention comprise substantially pure Spongilla powder. As used herein, "substantially pure" refers to a natural product, specifically a *Porifera* sp. that has been separated from environmental debris including rocks, sticks, other marine life etc., washed, dried, ground, sieved and sized.

The present inventor has determined through analysis and clinical research that harvesting conditions and formulation protocols are important in providing a reproducibly effective topical therapeutic. Fresh water sponges are easily identified by competently trained marine biologists possessing no more than ordinary skill. For example, when a fresh-water aquatic environment is observed Spongilla appears as dull creamy brown to medium brown amorphous bodies. Often times larger sponge colonies will appear greenish due to algae trapped within the sponges' bodies. Furthermore, evidence of sponge viability and bioactive compound excretion can be observed empirically and include such factors as the lack of algal overgrowth and low predation rate.

*Spongilla lacustris* is generally preferred for making the compositions of the present invention because this sponge genus is highly tolerate of natural environmental variation and grows extremely well in a wide range of habitats. In order to avoid collecting environmentally induced variants having less than ideal potency the present inventor has determined that *S. lacustris* is preferably collected at summer's end on warm sunny days. If sudden environmental changes occur which adversely affect sponge viability harvesting should be terminated.

Figure 1:
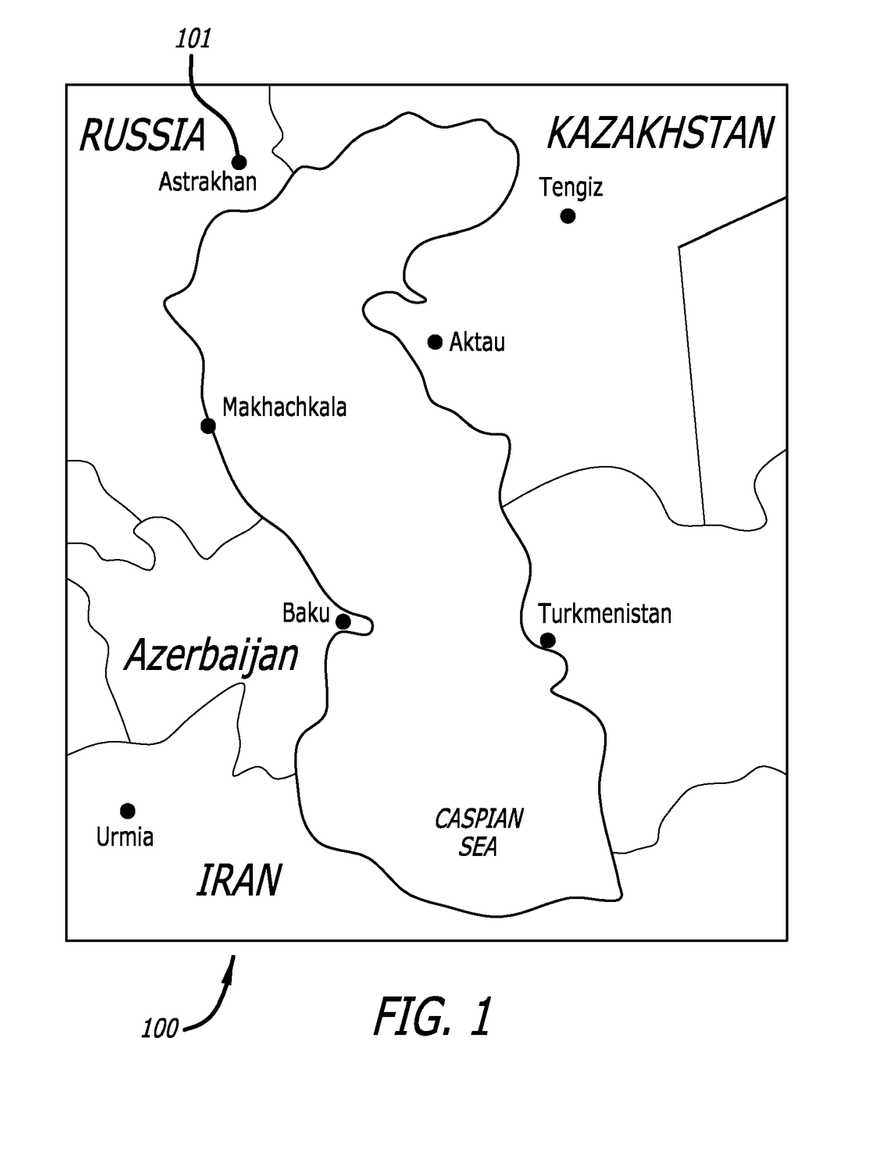
FIG. 1 depicts a specific geographical location where one species of the Porifera of the present invention can be harvested.

Aquatic environments favorable to *S. lacustris* production include an identifiable substratum having submerged rocks, sticks and branches. Generally, lakes are better natural habitats than rivers and streams for the development of large sponge colonies due to the absence of strong currents. In still waters such as lakes freshwater sponges form colonies ranging from 2.4 to 40 cm across in deer-horn-shape, finger- and bush-like forms. Water clarity is also an important environmental factor in supporting large, developed *Spongilla lacustris* colonies. Water clouded by dirt, mud and dissolved solids depress sponge growth thus reducing colony size and sponge quality. Consequently, muddy, cloudy and turbulent waters, as well as lakes having contaminated source waters should be avoided when selecting harvest locations. In one embodiment of the present invention *S. lacustris* is harvested from fresh water lakes in the Russian Federation northwest of the Caspian Sea, specifically Astrakhan region as depicted in FIG. 1 at 101.

Once an appropriate aquatic environment and sponge habitat is identified sponge collection can begin using methods commonly known to those skilled in the art of marine biology. For example, sponges can be collected manually using basic under water diving techniques, or in deeper waters larger colonies are harvested using the Agassiz trawl (AGT) or epibenthic sledge (EBS). However, sponges smaller than 0.5 cm in diameter are unlikely to be collected by AGT. Under certain environmental conditions *S. lacustris* colonies occur in a thin crust-like carpet several meters across and must be collected manually, with fork-like tools, and nets.

Freshly collected sponges removed from their aquatic habitat are mucoid amorphous masses and emit a characteristic odor that most observers describe as unpleasant. Before the collected sponge mass is dried it must be clean of gross contamination including portions of the substrata, shells, stems, plants, small fresh water animals, rocks and other impurities. Next the sponge mass is washed to remove dirt, sand, silt and soluble impurities. The wash water is changed repeatedly until it is clear and the sponges appear free from contamination. After removing gross debris and cleaning, the sponge mass is weighed and dried. Drying is preferable done in the open air on a warm clear day. However, commercial scale dryers used to dehydrate foods and pharmaceuticals can be used as appropriate. Generally, sponge harvesting is done in remote rural regions due to the difficulties associated with developing and sustaining artificial "sponge farm" habitats. Consequently, large commercial drying facilities are seldom available. As an alternative, collected sponge colonies can be sent to the repository, a low-temperature storage facility for their quarantine, delayed processing and further investigation.

When dried under ambient, open-air conditions temperature, dew point, relative humidity and forecasted precipitation must be closely monitored. If the ambient air temperature is too low or if precipitation is forecasted the sponge mass should be dried inside where temperature and humidity can be controlled. It is not essential that a precise temperature or humidity range be maintained, however, the sponge mass should be maintained within a temperature and humidity range suitable for an uninterrupted evaporative process to proceed. For example, temperatures should be above 60° F. and relative humidity should be below 90%. However, it is recommended that the sponge mass should be protected from exposure to atmospheric precipitation and excessive temperatures after collection. The sponge mass is dried until residual moisture content is less than 10%, preferably less than 5%. If the raw material is to be stored for protracted periods before further processing, residual moisture can be as low a 0.1% or less. Residual moisture measurements can be performed using methods commonly known in the arts of food sciences, analytical chemistry or the pharmaceutical sciences. For example, 10 grams of dried material is placed on a tared weighing boat and then weighed. The weighed material is then exposed to a heat source such as a drying oven or heat lamp operated at a temperature sufficient to evaporate any remaining free or loosely bound water (non-chemically bound). The sample is then cooled in a desiccated chamber and re-weighed. Residual moisture is calculated as the percent difference between the sample weight before drying and the weight after cooling.

Once dried, the sponge is packaged in sealed containers, protected from light and maintained in quarantine at 55° to 75° F. Routine quality control processes are conduced on the dried sponge material consistent with Good Manufacturing Practice Requirements (GMP) and International Standards Organization (ISO) regiments applicable to food, drugs and cosmetics before being released from quarantine and processed further. Testing includes microbiological culturing for pathogens, coliform organisms and bioburden. Chemical analysis is also performed to verify the product's identity, potency and purity. All processing after the initial drying phase should be conducted in environmentally controlled facilities that comply with GMP and ISO guidelines. Manufacturing personnel must be trained in GMP and ISO procedures and all manufacturing process closely monitored and recorded.

After release from quarantine the raw, dried material sponge is further refined and processed to a standard particle size using sieves. The dried sponge is extremely fragile and requires only slight, gentle grinding to form a consistently fine particulate. The dried sponges collected and processed in accordance with the teachings of the present invention should not be processed using aggressive grinding techniques, rather the dried sponge is processed gently to avoid crushing debris that may be present in the sample. For example, shells from aquatic mollusks may contaminate the crude sample; grinding of the crude sponge preparation should be conducted in a fashion that will not pulverize the contaminating shells to a degree that they would not be removed in the sieving processes. Several grinding and sieving steeps are performed to reduce average particle size to no more than 0.2 mm. First a course grind and sieving process is used to reduce particle size to at least 2 mm. This initial sieving process also permits visual inspection and removal of remaining non-sponge debris and is followed by subsequent grinding and sieving processes where the raw material is ultimately reduced to no more than 0.2 mm particles.

Next the sized material is ground and sieved again to reduce particle size to more than 0.2 mm. After the desiccated sponge powder is ground, it is further purified and separated from contaminates by processing the powder with sieves having progressively smaller apertures (1 mm, 0.5 mm, and 0.2 mm respectively). All processing is conducted under GMP conditions.

After final grinding and sizing processes are completed the dried sponge material is packaged in airtight moisture-proof containers and stored in the dark at 55° to 75° F. under desiccated conditions. No preservatives are required due to the natural antimicrobial properties of the Spongilla powder. Spongilla powder collected, processed and stored in accordance with the teachings of the present invention is stable for a minimum of three years and six months (stability data available as of the filing date of the instant patent). However, accelerated testing data may suggest much longer stability periods (up to 10 years).

The therapeutic compositions of the present invention comprise from approximately 0.1% to 100% substantially pure Spongilla powder and can optionally compounded with pharmaceutical excipients including, but not limited to water, saline, buffered phosphate, oils, gels, waxes, emollients, glycerin, cleansers, fragrances, colorings, antiseptics and anesthetics. Suitable waters include water for injection, irrigation water, distilled water, deionized water, and floral water among others. Even clean tap water is acceptable for some applications. The concentrations of the aforementioned excipients can range from 0.001% to 50% or more depending on the requirements and at the discursion of the formulation scientist, pharmacist or prescribing physician. Such ranges are well known in the art and can be determined without undue experimentation. Other excipients that may be used in accordance with the teachings of the present invention may include from approximately 0.1% to 25% coral powder, from approximately 0.1% to 25% seaweed powder, from approximately 0.1% to 10% hydrogen peroxide and from approximately 0.1 to 10% of an inorganic or organic acid such as, but not limited to boric acid, hydrochloric, ascorbic acid, salicylic acid, and others.

The therapeutic compositions of the present invention generally comprise from 0.8 to 1.5 grams of substantially pure Spongilla powder, and at least one additional excipient selected from the group consisting of from 0.1 to 0.5 grams of green seaweed powder, from 0.1 to 0.5 grams of white seaweed powder, from 0.1 to 0.5 grams of coral powder, from 0.1 to 0.5 grams of Plantain powder, from 0.5 mL to 5 mL of 0.1% to 10% hydrogen peroxide, from 0.5 mL to 5 mL of 0.1% to 10% boric acid and from 0.5 to 5 mL of water, from 0.5 mL to 5 mL enzyme gel (comprising water, hydroxyethylcellulose, hyaluronic acid, propylene glycol, methylparaben, tetrasodium EDTA and propylparaben in proportions suitable for topical applications as known to those skilled in the art), from 0.5 mL to 10 mL jojoba oil. Other excipients such as, but not limited to saline, buffered phosphate, oils, waxes, emollients, glycerin, cleansers, fragrances, colorings, antiseptics and anesthetics may be added as desired or required.

EXAMPLES

The following examples provide formulations using exact amounts in grams and milliliters of each ingredient. However, these exact weights and volumes should not be considered limitations. All of the liquids used herein are aqueous based and contain low percentages of solute. Therefore, the relative weight of each volume of liquid ingredient will be considered equal to the weight of water (1 g/mL). The appended claims will therefore be expressed as ratios. For example, a composition made in accordance with the teachings of the presently invention may contain 1.5 g of substantially pure Spongilla powder, 0.5 mL hydrogen peroxide, 2 mL of 5% boric acid, 1 gram of green sea weed powder and 10 mL of floral water. This composition would then be claimed as follows: 1.5 parts of substantially pure Spongilla powder, 0.5 parts 3% hydrogen peroxide, 2 parts of 5% boric acid, 1 part of green sea weed powder and 10 parts of floral water; etc.

Example 1

Basic Topical Acne Treatment

Therapeutic compositions prepared from the dried Spongilla powder can be prepared using formulating excipients and procedures known to those skilled in the art of topical medicament preparation. For example, in one embodiment of the present invention topical acne therapeutic comprises of 1.0 grams of Spongilla powder (active ingredient) and 2.0 milliliter of 3% hydrogen peroxide (vehicle). The ingredients are combined and mixed together. The mixture then is heated in the microwave for about 7 seconds. During heating hydrogen peroxide transforms into water and oxygen, which results in fluffy mask of homogeneous consistency. The therapeutic is then applied to the entire face in massaging circular motions, left on for 15 to 30 minutes, and then washed off with water. Recommended usage is every 5 to 7 days.

Example 2

Topical Acne Treatment for Professional Use

In another embodiment of the present invention, topical acne therapeutic comprises of 1.5 grams of Spongilla powder, 1.0 milliliter of 3% hydrogen peroxide, and 3.0 milliliters of 5% boric acid. The mixture and application of this topical anti-acne composition for professional use includes mixing the powder with warm liquids just before use. The therapeutic is then applied to the face or other affected area in circular motions, left on for 25 to 30 minutes, and then washed off with water. Recommended usage is every 4 to 5 days.

Example 3

Topical Acne Composition for Home Use

In one embodiment of the present invention topical acne therapeutic for home use comprises 0.8 grams of Spongilla powder, 0.2 grams of Plantain powder and 2.5 milliliters of enzyme gel. The mixture and application of this topical anti-acne composition for home use includes mixing the powder with liquid just before use. The contents are then applied to the face or other affected area with a brush, left to dry for 15 minutes and then washed off with water. Recommended usage is every day for a week or until face is cleared and then once a week for maintenance.

Example 4

Professional Skin Resurfacing Composition

Formulas suitable for professional skin resurfacing comprise of 1.5 grams of Spongilla powder, 0.2 grams of green seaweed powder, 5.0 milliliters of 3% hydrogen peroxide. The mixture and application of this professional skin resurfacing formula includes mixing the powder with hot liquid just before use. The contents are then applied to the face or other affected area in a circular motion for approximately 5 minutes. Mixture is than left to dry for 25 to 30 minutes and then washed off with water. Recommended usage is once a week.

Example 5

Topical Oily Skin Treatment

Formulas for treatment of oily skin may comprise 1.0 grams of Spongilla powder and 2.0 milliliters of chamomile, menthol or calendula water. The mixture and application of this professional skin resurfacing formula includes mixing the powder with warm liquids just before use. The contents are left on for 5 to 10 minutes and then washed off with water. Recommended usage is every 2 days until sebum production is suppressed and then every 10 days for maintenance.

Example 6

Topical Deep Peeling Skin Treatment

Formulas for deep peeling of the skin may comprise of 1.5 grams of Spongilla powder, 0.3 grams of green seaweed powder, and 5.0 milliliters of 4% hydrogen peroxide. The mixture and application of this professional deep peeling formula includes a 7 day process. On the first day, the face or effected area is to be steamed. The powder is mixed with hot liquid just before use. The contents are then applied to the face or other affected area in a circular motion. After 5 to 6 minutes, a mask is saturated with hydrogen peroxide in circular motions. It is left to dry for 20 minutes and washed off with water. On day 2, the face or effected area is washed with 2% salicylic acid. The contents are then applied to the face or other affected area in a circular motion. After 5 to 6 minutes, a mask is saturated with hydrogen peroxide in circular motions. It is left to dry for 20 minutes and washed off with water. On the third and fourth days boric ointment is applied to effected areas. On the fifth and sixth days, a moisturizer and soothing mask is applied. On the seventh and last day of treatment, the effected area is exfoliated with a scrub. Recommended usage is once a month.

Example 7

Treatment of Hyperpigmentation Disorders

Formulas for hyperpigmented spots removal (including but not limited to melasma, age spots, sun-damage, etc.) of the skin may comprise of 1.0 grams of Spongilla powder, 0.2 grams of white seaweed powder and 3.0 milliliters of enzyme gel. The contents are then mixed together and applied to the face or other affected area in massaging circular motions for approximately 10 minutes, left to dry for 25 to 30 minutes and then washed off with water. Recommended usage is twice a week.

Example 8

Treatment for Photo-Damaged and Aging Skin

Formulas for photo-damaged skin may comprise of 2.0 grams of Spongilla powder and 5.0 milliliters of jojoba oil. The mixture and application of this formula for photo-damaged and aging skin includes mixing the powder with hot oil just before use. The contents are then massaging into the face or other affected in circular motions for 30 to 45 minutes, left to stay for 25 to 30 minutes and then washed off with water. Recommended usage is once a week.

Example 9

Treatment for Seborrhoeic Dermatitis of the Scalp

Formulas for seborrhoeic dermatitis of the scalp comprise 5.0 grams of Spongilla powder, 5.0 milliliters of 3% of hydrogen peroxide and 5.0 milliliters of 2% of boric acid. The mixture and application of this professional skin resurfacing formula includes mixing the powder with hot liquids just before use. The contents are then applied to the affected area in a circular massaging motion. Mixture is than left for 30 minutes and then washed off with water. Recommended usage 5 to 6 days for 8-10 weeks and then, once a month for maintenance.

The preceding exemplary embodiments are not intended as limitations and the Porifera compositions of the present invention may be formulated in myriad ways and still be considered within the scope of the present invention. The present inventor believes that desiccated Spongilla powdered comprises numerous biologically active compounds beneficial to promoting skin health, promoting healing and reducing scarring. These beneficial compounds include, but may not be limited to antibacterial, anti-inflammatory, antiviral and other organic bioactive agents in addition to inorganic compounds such as iodine, bromine, phosphorus and sulfur.

The exact mechanism of action of the Spongilla compositions of the present invention remains unknown. Moreover, the present inventor believes that the natural combination of ingredients contribute to a synergistic effect that may be destroyed or significantly reduced by extraction and purification of the aforementioned active ingredients. However, the present inventor has demonstrated safety and efficacy of the present invention as detailed in the following, non-limiting disclosure.

Safety Testing

I. In vivo Rabbit Tests

The test article, Desiccated Animal Sponge-Thistle, Batch: San Pin 2.3.2.560-96, was evaluated for primary skin irritation in accordance with the guidelines of the International Organization for Standardization 10933: Biological Evaluation of Medical Devices, Part 10: Tests for Irritation and Sensitization. Two 0.2 g portions of the test article moistened with 5 drops of 0.9% sodium chloride and vehicle control article were topically applied to the skin of each of three rabbits and left in place for 24 hours. The sites were graded for erythema and edema at 1, 24, 48 and 72 hours after removal of the single sample application. Under the conditions of this study, no erythema and no edema were observed on the skin of the rabbits. The Primary Irritation Index for the test article was calculated to be 0.0. The response of the test article was categorized as negligible.

The test article identified below was evaluated for primary skin irritation in accordance with the guidelines of the International Organization for Standardization 10933: Biological Evaluation of Medical Devices, Part 10: Tests for Irritation and Sensitization. The purpose of this study was to determine the potential for a single topical application of the test article to irritate skin of the rabbit. The test article was received on Aug. 30, 2002. Patches were applied on Sep. 5, 2002, and the observations wee concluded on Sep. 9, 2002 was conducted in accordance with the provisions of the FDA Good Laboratory Practice (GLP) Regulations, 21 CFR 58.

Materials

| | |
|---|---|
| Test Article: | Desiccated Animal Sponge-Thistle |
| Identification No.: | Batch: San Pin 2.3.2.506-96 |
| Stability Testing: | Complete and on file with the sponsor (per sponsor) |
| Expiration Date: | April, 2004 |
| Vehicle: | 0.9% Sodium Chloride, sterile saline |
| Storage Conditions: | Dry, dark conditions: |
| Control Article: | Four-ply gauze supplied by the test facility, was cut into 25 mm × 25 mm sections and moistened with 5 drops of 3% hydrogen peroxide per section. |
| Preparation: | 0.2 gram portion of the test article (weighted by sponsor prior to submission), Desiccated Animal Sponge-Thistle, was moistened with 5 drops of 0.9% sodium chloride. The test article and saline were mixed to form a paste consistency. The test mixture was applied to the animals' skin and allowed to air dry for 20 minutes, then wrapped with 4-ply gauze. |
| Test System: | Male Rabbits (*Oryctolagus Cuniculus*) New Zealand |

Experimental Procedure

On the day prior to treatment, the fur on each rabbit's back was clipped with an electric clipper. On the day of treatment, four sites, two on each side of the back and positioned cranially and caudally, were designated on each rabbit. The sites were free of blemishes that could interfere with the interpretation of results.

A 0.2 g portion of the test article was moistened with 5 drops of saline, and applied to each caudal site (two sites per rabbit) approximately 25 mm×25 mm square. The test article mixture was allowed to air dry for 20 minutes prior to wrapping. The control vehicle was similarly applied to the caudal sites. The trunk of each animal was wrapped with an elastic binder to maintain the test patches in position. Animals were returned to their cages after treatment.

After the 24 hour exposure, the binders, tape, and patches were removed. The sites were gently wiped with a gauze sponge dampened with deionized water in an attempt to remove any remaining residue. Dermal observations for erythema and edema were recorded at 1, 24, 48 and 72 hours after patch removal.

The Primary Irritation Index of the test was calculated following test completion for each animal. The erythema and edema scores obtained at the 24, 48 and 72 hour intervals were added together and divided by the total number of observations. This calculation was conducted separately for the test and control article for each animal. The score for the control was subtracted from the score for the test article to obtain the Primary Irritation Score. The Primary Irritation Score (see Table 2) for each rabbit was added together and divided by the number of rabbits to obtain the Primary Irritation Index (see Table 3).

Results

No irritation was observed on the skin of the rabbits as summarized in Table 1. The Maximum Irritation Response was not applicable. The Primary Irritation Index of the test article was calculated to be 0.0. The irritation calculations are shown below:

TABLE 1

| Rabbit Number | Test Score Average | Control Score Average | Individual Primary Irritation Score | Combined Primary Irritation Score (CPIS) | Primary Irritation Index (CPIS ÷ 3) | Response Category |
|---|---|---|---|---|---|---|
| 65977 | 0.0 | 0.0 | 0.0 | 0.0 | 0.0 | Negligible |
| 65976 | 0.0 | 0.0 | 0.0 | | | |
| 65975 | 0.0 | 0.0 | 0.0 | | | |

TABLE 2

Classification System for Skin Reaction

| Reaction | NUMERICAL GRADING |
|---|---|
| Erythema and Eschar Formation | |
| No erythema | 0 |
| Very slight erythema (barely perceptible) | 1 |
| Well-defined erythema | 2 |
| Moderate erythema | 3 |
| Severe erythema (beet redness) to eschar formation preventing grading of erythema | 4 |
| Edema Formation | |
| No edema | 0 |
| Very slight edema (barely perceptible) | 1 |
| Well-defined edema (edges of area well-defined by definite raising) | 2 |
| Moderate edema (raised approximately 1 mm) | 3 |
| Severe edema (raised more than 1 mm and extending beyond exposure area) | 4 |
| Total possible score for irritation | 8 |

NOTE:
Other adverse changes at the skin sites shall be recorded and reported

TABLE 3

Irritation Response Categories in the Rabbit

| RESPONSE CATEGORY | MEAN SCORE |
|---|---|
| Negligible | 0.0 to 0.4 |
| Slight | 0.5 to 1.9 |
| Moderate | 2.0 to 4.9 |
| Severe | 5.0 to 8.0 |

Safety Testing:Conclusion

Under the conditions of this study, no erythema and no edema were observed on the skin of the rabbits. The Primary Irritation Index for the test article was calculated to be 0.0. The response of the test article was categorized as negligible.

II. In vivo Guinea Pig Tests

The test article described below was evaluated for the potential to cause delayed dermal contact sensitization following repeated occlusive patching in the guinea pig. The study was conducted based on the requirements of the International Organization for Standardization 10993: Biological Evaluation of Medical Devices, Part 10: Tests for Irritation and Sensitization. The test article was received on Aug. 30, 2002. The first patch was applied on Sep. 17, 2002, and the observations were concluded on Oct. 22, 2002. The susceptibility of the Hartley guinea pig strain to a known sensitizing agent, 1-chloro-2,4-dinitrobenzene (DNCB), has been substantiated.

The study was conducted in accordance with the provisions of the FDA Good Laboratory Practice (GLP) Regulations, 21 CFR 58

Materials

| | |
|---|---|
| Test Article: | Desiccated Animal Sponge-Thistle |
| Identification No: | Batch: San Pin 2.3.2.560-96 |
| Stability Testing: | Complete and on file with the sponsor (per sponsor) |
| Expiration Date: | April, 2004 |
| Storage Conditions: | Dry, dark conditions |
| Control Article: | Approximate 25 mm × 25 mm sections of 4-ply gauze were used as the vehicle. |
| Preparation: | A 0.2 gram portion of the test article (weighed by sponsor prior to submission), Desiccated Animal Sponge-Thistle, was moistened with 5 drops of 3% hydrogen peroxide. The test article and hydrogen peroxide were mixed to form a paste consistency. The 0.2 grain portion of test article mixture was used for approximately 5 patches applied to the animals' skin. The test mixture was allowed to air dry for 20 minutes, then wrapped with 4-ply gauze. |
| Species: | Female Guinea pig (*Cavia porcellus*) Crl:(HA) Charles River Laboratories Body Weight Range: 311 grams to 366 grams the day prior to first treatment |

The Hartley albino guinea pig has been used historically for sensitization studies. Repeated patching of the test material to fur-clipped intact skin will be employed. Topical applications are related to the human exposure route and will permit the evaluation of dermal contact and/or absorption of potential sensitizers during induction and challenge phases. Reactions directly under the topical application site can be observed. The susceptibility of the Hartley strain to a known sensitizing agent, 1-chloro-2,4-dinitrobenzene (DNCB), has been substantiated.

Experimental Procedure

On the day prior to the first induction treatment, each animal was weighed and identified. The hair was removed with an electric clipper from the left flank of 10 guinea pigs designated as test animals and 5 guinea pigs designated as control animals. Each animal was observed daily for general health.

The following day, an aliquot of the test mixture was applied to an approximate 25 mm×25 mm area of the appropriate animals. The test mixture was allowed to dry for 20 minutes before wrapping. The patch was then secured with hypoallergenic tape to the intact skin. To maintain the occluded patch in position, the trunk of each guinea pig was wrapped with an elastic band.

At 6 to 8 hours, the wraps and patches were removed. The sites were wiped with dry gauze after patch removal to remove any material residue from the skin. Observations for dermal responses were recorded 24 hours following the completion of each test article exposure. Prior to scoring, the sites were wiped with 35% isopropyl alcohol saturated gauze.

The application procedure was repeated three times each week (e.g. Monday-Wednesday-Friday) for 3 weeks until nine applications were made to the left flank of the animals. The hair was clipped the day prior to each application to provide a clear site.

At 13 days after the final induction patch, the hair of each guinea pig was removed with an electric clipper from the right flank area. On the following day, an approximate 25 mm×25 mm section of both the control and test article was applied to the intact skin on the dorsal and ventral regions of the right flank of each test and control guinea pig. The trunk of each guinea pig was wrapped with an elastic band to hold the occluded patch in place.

All wraps and patches were removed 6 to 8 hours later. The sites were wiped with dry gauze after patch removal. At 24 hours after patch removal, the challenged sites and surrounding area were shaved. Observations for dermal reactions were conducted at 2-4 hours following the shave and at 48 and 72 hours after challenge patch removal. Sites were wiped with 35% isopropyl alcohol saturated gauze before scoring at each interval. Evaluations for both the induction and challenge phases were based on dermal reactions which were scored as outlined below in Table 4.

TABLE 4

Dermal Reactions

| ERYTHEMA (ER) | | EDEMA (ED) | |
| --- | --- | --- | --- |
| Reaction | Numerical Grading | Reaction | Numerical Grading |
| No erythema | 0 | No edema | 0 |
| Slight erythema | 1 | Slight edema | 1 |
| Well-defined erythema | 2 | Well-defined edema | 2 |
| Moderate erythema | 3 | Moderate edema | 3 |
| Severe erythema to slight eschar formation | 4 | Severe edema | 4 |

Following the challenge patch, any test animal exhibiting a dermal reaction greater than that observed in the challenge control conditions was considered as showing delayed contact sensitization to the test article. Pattern and duration of reactions was also considered in the final evaluation.

Results

Clinical Observations: Individual body weights are presented in Appendix 1. All animals appeared clinically normal throughout the study.

Dermal Observations: Individual results of dermal scoring for the induction and challenge phases appear in Tables 5 and 6. No evidence of sensitization was observed. All procedures were conducted in conformance with good laboratory practice and ISO 17025.

TABLE 5

Individual Body Weights and Clinical Observations

| | Individual Observation | |
| --- | --- | --- |
| Animal Number/ Group | Pretreatment Body Weight (g) | Clinical Observations |
| 1 Test | 327 | Appeared normal |
| 2 Test | 354 | Appeared normal |
| 3 Test | 325 | Appeared normal |
| 4 Test | 311 | Appeared normal |
| 5 Test | 344 | Appeared normal |
| 6 Test | 333 | Appeared normal |
| 7 Test | 324 | Appeared normal |
| 8 Test | 333 | Appeared normal |
| 9 Test | 343 | Appeared normal |
| 10 Test | 334 | Appeared normal |
| 11 Control | 366 | Appeared normal |
| 12 Control | 347 | Appeared normal |
| 13 Control | 325 | Appeared normal |
| 14 Control | 355 | Appeared normal |
| 15 Control | 329 | Appeared normal |

Safety Testing:Conclusion

Under the conditions of this study, the Spongilla therapeutic compositions of the present invention did not show any evidence of delayed dermal contact sensitization in the guinea pig. Thus, when Spongilla preparations are prepared in accordance with the teachings of the present invention there are no demonstrable toxic and allergic reactions induced in the recipient.

TABLE 6

Guinea Pig Sensitization Dermal Reactions - Induction

| Animal Number/ Group | Induction Patch Number | | | | | | | | | | | | | | | | | |
| --- | --- | --- | --- | --- | --- | --- | --- | --- | --- | --- | --- | --- | --- | --- | --- | --- | --- | --- |
| | 1 | | 2 | | 3 | | 4 | | 5 | | 6 | | 7 | | 8 | | 9 | |
| | ER | ED | ER | ED | ER | ED | ER | ED | ER | ED | ER | ED | ER | ED | ER | ED | ER | ED |
| Test | 0 | 0 | 0 | 0 | 0 | 0 | 0 | 0 | 0 | 0 | 0 | 0 | 0 | 0 | 0 | 0 | 0 | 0 |
| 2 Test | 0 | 0 | 0 | 0 | 0 | 0 | 0 | 0 | 0 | 0 | 0 | 0 | 0 | 0 | 0 | 0 | 0 | 0 |

TABLE 6-continued

Guinea Pig Sensitization Dermal Reactions - Induction

| Animal Number/ Group | Induction Patch Number | | | | | | | | | | | | | | | | | |
|---|---|---|---|---|---|---|---|---|---|---|---|---|---|---|---|---|---|---|
| | 1 | | 2 | | 3 | | 4 | | 5 | | 6 | | 7 | | 8 | | 9 | |
| | ER | ED | ER | ED | ER | ED | ER | ED | ER | ED | ER | ED | ER | ED | ER | ED | ER | ED |
| 3 Test | 0 | 01 | 0 | 0 | 0 | 0 | 0 | 0 | 0 | 0 | 0 | 0 | 0 | 0 | 0 | 0 | 0 | 0 |
| 4 Test | 0 | 0 | 0 | 0 | 0 | 0 | 0 | 0 | 0 | 0 | 0 | 0 | 0 | 0 | 0 | 0 | 0 | 0 |
| 5 Test | 0 | 0 | 0 | 0 | 0 | 0 | 0 | 0 | 0 | 0 | 0 | 0 | 0 | 0 | 0 | 0 | 0 | 0 |
| 6 Test | 0 | 0 | 0 | 0 | 0 | 0 | 0 | 0 | 0 | 0 | 0 | 0 | 0 | 0 | 0 | 0 | 0 | 0 |
| 7 Test | 0 | 0 | 0 | 0 | 0 | 0 | 0 | 0 | 0 | 0 | 0 | 0 | 0 | 0 | 0 | 0 | 0 | 0 |
| 8 Test | 0 | 0 | 0 | 0 | 0 | 0 | 0 | 0 | 0 | 0 | 0 | 0 | 0 | 0 | 0 | 0 | 0 | 0 |
| 9 Test | 0 | 0 | 0 | 0 | 0 | 0 | 0 | 0 | 0 | 0 | 0 | 0 | 0 | 0 | 0 | 0 | 0 | 0 |
| 10 Test | 0 | 0 | 0 | 0 | 0 | 0 | 0 | 0 | 0 | 0 | 0 | 0 | 0 | 0 | 0 | 0 | 0 | 0 |
| 11 control | 0 | 0 | 0 | 0 | 0 | 0 | 0 | 0 | 0 | 0 | 0 | 0 | 0 | 0 | 0 | 0 | 0 | 0 |
| I2 Control | 0 | 0 | 0 | 0 | 0 | 0 | 0 | 0 | 0 | 0 | 0 | 0 | 0 | 0 | 0 | 0 | 0 | 0 |
| I3 Control | 0 | 0 | 0 | 0 | 0 | 0 | 0 | 0 | 0 | 0 | 0 | 0 | 0 | 0 | 0 | 0 | 0 | 0 |
| I4 Control | 0 | 0 | 0 | 0 | 0 | 0 | 0 | 0 | 0 | 0 | 0 | 0 | 0 | 0 | 0 | 0 | 0 | 0 |
| I5 Control | 0 | 0 | 0 | 0 | 0 | 0 | 0 | 0 | 0 | 0 | 0 | 0 | 0 | 0 | 0 | 0 | 0 | 0 |

Test = Test article
Control = Control article
ER = Erythema
ED = Edema

TABLE 7

Dermal Reactions - Challenge

| Animal Number/ Group | Hours After Patch Removal | | | | | | | | | | | |
|---|---|---|---|---|---|---|---|---|---|---|---|---|
| | 24 | | | | 48 | | | | 72 | | | |
| | Test Site | | Control Site | | Test Site | | Control Site | | Test Site | | Control Site | |
| | ER | ED | ER | ED | ER | ED | ER | ED | ER | ED | ER | ED |
| 1 Test | 0 | 0 | 0 | 0 | 0 | 0 | 0 | 0 | 0 | 0 | 0 | 0 |
| 2 Test | 0 | 0 | 0 | 0 | 0 | 0 | 0 | 0 | 0 | 0 | 0 | 0 |
| 3 Test | 0 | 0 | 0 | 0 | 0 | 0 | 0 | 0 | 0 | 0 | 0 | 0 |
| 4 Test | 0 | 0 | 0 | 0 | 0 | 0 | 0 | 0 | 0 | 0 | 0 | 0 |
| 5 Test | 0 | 0 | 0 | 0 | 0 | 0 | 0 | 0 | 0 | 0 | 0 | 0 |
| 6 Test | 0 | 0 | 0 | 0 | 0 | 0 | 0 | 0 | 0 | 0 | 0 | 0 |
| 7 Test | 0 | 0 | 0 | 0 | 0 | 0 | 0 | 0 | 0 | 0 | 0 | 0 |
| 8 Test | 0 | 0 | 0 | 0 | 0 | 0 | 0 | 0 | 0 | 0 | 0 | 0 |
| 9 Test | 0 | 0 | 0 | 0 | 0 | 0 | 0 | 0 | 0 | 0 | 0 | 0 |
| 10 Test | 0 | 0 | 0 | 0 | 0 | 0 | 0 | 0 | 0 | 0 | 0 | 0 |
| 11 Control | 0 | 0 | 0 | 0 | 0 | 0 | 0 | 0 | 0 | 0 | 0 | 0 |
| 12 Control | 0 | 0 | 0 | 0 | 0 | 0 | 0 | 0 | 0 | 0 | 0 | 0 |
| 13 Control | 0 | 0 | 0 | 0 | 0 | 0 | 0 | 0 | 0 | 0 | 0 | 0 |
| 14 Control | 0 | 0 | 0 | 0 | 0 | 0 | 0 | 0 | 0 | 0 | 0 | 0 |
| 15 Control | 0 | 0 | 0 | 0 | 0 | 0 | 0 | 0 | 0 | 0 | 0 | 0 |

ER = Erythema
ED = Edema

Exemplary Method for Using the Porifera Compositions of the Present Invention

Introduction:

A pre-weighed package containing substantially pure Spongilla powered is provided. The pre-weighed amount is sufficient for one application to the face. Alternatively, this application can be used to treat the chest, neck, or shoulders instead of face. The treatment may be performed by a medical doctor, a nurse or patient, trained in the procedure. It can be safely administered to patients of all skin types.

The patient should be informed to avoid unprotected sun exposure for two weeks prior to each treatment. Products such as glycolic acid (over-the counter-strength), Retin-A, and Renova should be discontinued for at least 14 days prior to treatment. A longer period of time (several months) must be allowed to pass following professional strength glycolic acid, Jessner's, phenol and TCA peels; $CO_2$ laser resurfacing and Erbium laser peels. However, in medical office each case may be examined individually.

The treatment areas should be washed with a mild cleanser after make-up is removed. The person performing the procedure may wear protective gloves (it is not a requirement).

Treatment Preparation:

Measure out two milliliters of 3% hydrogen peroxide into a small (about 30 ml-50 ml) non-metal container. Gently heat in a microwave to bring the solution to a lukewarm temperature. Using a 1300 watt microwave, time setting is usually 2-10 seconds depending on whether the container is glass or plastic. Pour the warmed peroxide solution into the pre-weighed container of Spongilla powder. Gently stir to obtain a thin paste of fairly homogeneous consistency. Alternatively, the powder can be mixed with the hydrogen peroxide first and then warm.

Treatment Application:

Apply one quarter of the amount to the mid-forehead by massaging in circular motions. Spread the paste gently with your fingertips in small circular movements up to the hairline using even pressure. As this paste begins to dry, repeat the same steps as you move down the temples, cheeks, nose and chin. Mild to moderate erythema usually develops. A sensation of sharp crystal needles under the skin is commonly experienced during application. It is best to avoid the periorbital area because the skin is thinner and more sensitive. It is extremely important to massage the paste into the skin before it dries to optimize penetration of active ingredients into the skin. This may take 5 minutes for the face. The neck and chest should always be done last. The most comfortable way to rinse the face is to have the patient splash cold water rather than to wipe their face with a wet washcloth. The skin erythema and tingling sensation of the skin gradually fades over the following 12-24 hours.

| Recommended Treatment Times* | |
|---|---|
| | Total Suggested Time |
| Face | 10-30 minutes |
| Neck | 5-20 minutes |
| Chest | 5-20 minutes |

*Treatment times may vary. Stop immediately if the patient experiences pain and discomfort. Wash the skin with cool water immediately.

Instruct the patient to use a sunscreen with SPF 30-40, preferably one with zinc to help soothe the skin, for at least 2 weeks after each treatment. Explain that failure to do so may result in hyperpigmentation. For the best results, the patient should avoid applying a moisturizer for at least 12 hours. Rich moisturizers should be avoided during the course of treatment. Use of powder make-up or a light foundation can be resumed after the first 12 hours. All patients must be instructed to do the exfoliating on the $5^{th}$-$6^{th}$ day at home with scrub provided or return to the office for exfoliating procedure.

Efficacy Testing

Figure 2:
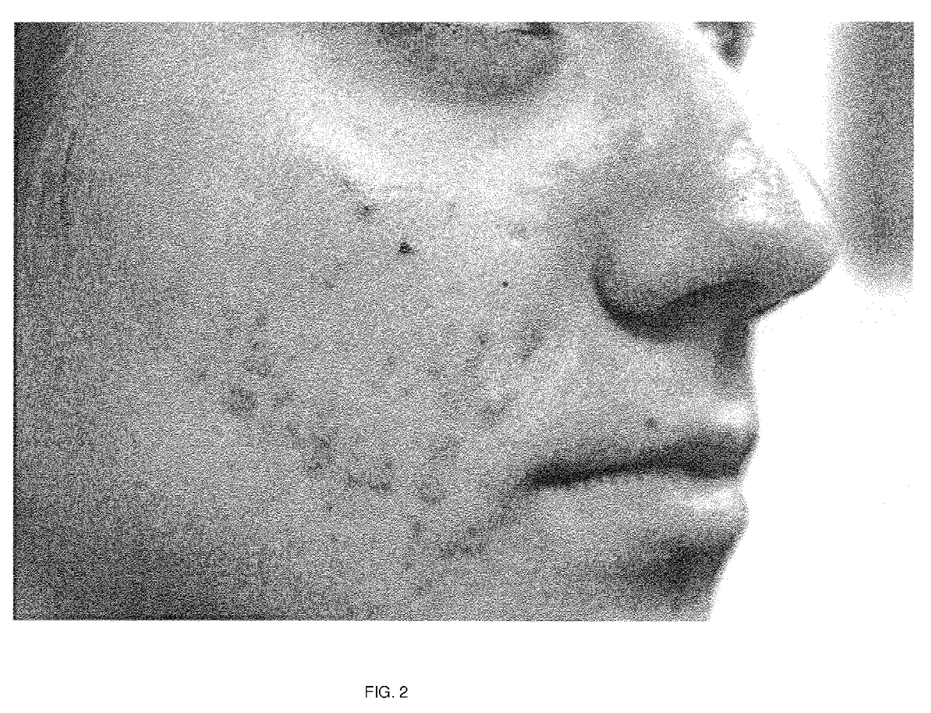
FIG. 2 depicts a patient before receiving treatment for acne in accordance with the teachings of the present invention
Figure 3:
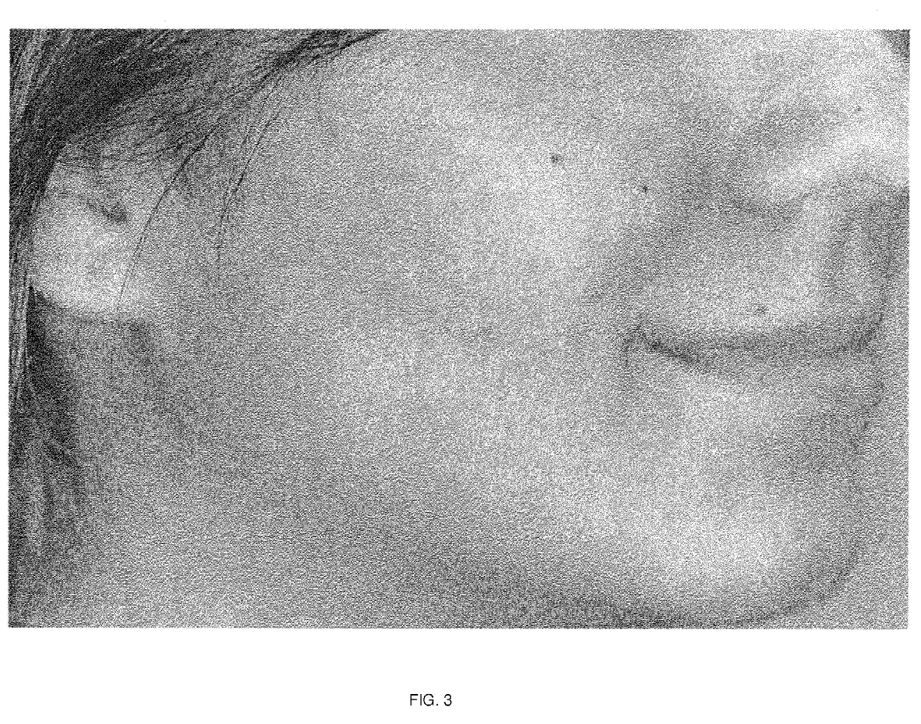
FIG. 3 depicts the patient in FIG. 2 after receiving treatment for acne in accordance with the teachings of the present invention

In one embodiment of the present invention a patient, depicted in FIG. 2 was treated using the therapeutic compositions prepared from the dried Spongilla powder and formulated as disclosed above. More specifically, the topical therapeutic was formulated as a topical acne therapeutic comprising of 1.0 grams of Spongilla powder and 2.0 milliliter of 3% hydrogen peroxide mixed prior to use and heated in the microwave for 7 seconds. The topical composition was applied to the entire face with circular motions under the supervision of a trained physician. The treatment was left in contact with the patient's skin for 25 minutes, and then washed off with water. This treatment protocol was repeated every 7 days for 4 weeks. After treatment was completed the patient appears as depicted in FIG. 3.

The therapeutic compositions of the present invention are derived from Porifera species and can be used to treat myriad skin diseases and disorders. Specifically, the present invention provides Spongilla-derived topical therapeutics effective in the treatment of acne vulgaris, rosacea, seborrheic dermatitis, eczema (atopic dermatitis), psoriasis, photo-aging, actinic keratosis, and great number of other bacterial, viral, and fungal diseases as well as skin pigmentation disorders. Several exemplary embodiments are provided; however, it is understood by those skilled in the art of pharmaceutical compounding that many other compositions are possible without departing from the spirit of the claimed invention.

Unless otherwise indicated, all numbers expressing quantities of ingredients, properties such as molecular weight, reaction conditions, and so forth used in the specification and claims are to be understood as being modified in all instances by the term "approximately." Accordingly, unless indicated to the contrary, the numerical parameters set forth in the following specification and attached claims are approximations that may vary depending upon the desired properties sought by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illustrate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. A method of treating skin diseases comprising: applying to the skin of an individual a therapeutic composition consisting of a substantially pure powder of a fresh water sponge, *Spongilla lacustris*, and at least one pharmaceutically acceptable excipient, wherein the substantially pure powder consists of approximately 50% to 60% insoluble material obtained from *S. lacustris* having a maximum particle size of 0.2 mm, wherein the therapeutic composition treats the skin condition.

2. The method according to claim 1, wherein the skin disease is selected from the group consisting of: acne vulgaris, rosacea, seborrheic dermatitis, atopic dermatitis, psoriasis, photo-aging, and actinic keratosis.

3. The method according to claim 1, wherein the *S. lacustris* is harvested from the Arstrakian region of the Russian Federation.

4. The method of claim 1, wherein the pharmaceutically acceptable excipient is selected from the group consisting of: water, glycerin, gels, oils, waxes, emollients, cleansers, fragrances, antiseptics, anesthetics, seaweed powder, coral powder, plantain powder, hydrogen peroxide, enzyme gel, jojoba oil, and boric acid.

5. The method of claim 1, wherein the composition abrades-the skin of the individual.

6. The method of claim 1, wherein the method results in resurfacing of the skin of the individual.

7. The method of claim 1, wherein the therapeutic composition is massaged into the skin such that spicules contained in the substantially pure powder of *S. lacustris* penetrate the upper layer of epidermis.

8. The method of claim 1, wherein the method results in debriding of the skin of the individual.

9. The method of claim 1, wherein the method results in increased cell turnover of the skin of the individual.

10. The method according to claim 4, wherein the therapeutic composition consists of substantially pure powder of *S. lacustris* and 3% hydrogen peroxide.

11. The method of claim 4, wherein the water is selected from the group consisting of: water for injection, irrigation water, distilled water, deionized water, and floral water.

* * * * *